(12) United States Patent
Uchida et al.

(10) Patent No.: US 11,147,856 B2
(45) Date of Patent: Oct. 19, 2021

(54) HOT FLASH-SUPPRESSING AGENT

(71) Applicant: MEIJI CO., LTD., Tokyo (JP)

(72) Inventors: Masayuki Uchida, Odawara (JP); Orie Kobayashi, Odawara (JP)

(73) Assignee: MEIJI CO., LTD., Tokyo (JP)

( * ) Notice: Subject to any disclaimer, the term of this patent is extended or adjusted under 35 U.S.C. 154(b) by 286 days.

(21) Appl. No.: 15/560,791

(22) PCT Filed: Apr. 6, 2016

(86) PCT No.: PCT/JP2016/061265
§ 371 (c)(1),
(2) Date: Sep. 22, 2017

(87) PCT Pub. No.: WO2016/163400
PCT Pub. Date: Oct. 13, 2016

(65) Prior Publication Data
US 2018/0078610 A1    Mar. 22, 2018

(30) Foreign Application Priority Data

Apr. 7, 2015   (JP) .............................. JP2015-078574

(51) Int. Cl.
| | |
|---|---|
| *A61K 38/38* | (2006.01) |
| *A61P 15/12* | (2006.01) |
| *A61K 38/17* | (2006.01) |
| *A23L 33/19* | (2016.01) |
| *A23L 2/52* | (2006.01) |
| *A23L 2/66* | (2006.01) |

(52) U.S. Cl.
CPC ............ *A61K 38/1709* (2013.01); *A23L 2/52* (2013.01); *A23L 2/66* (2013.01); *A23L 33/19* (2016.08); *A61K 38/38* (2013.01); *A61P 15/12* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2005/0089546 A1* | 4/2005 | Wurtman | ............... | A61K 31/70 424/439 |
| 2005/0250793 A1 | 11/2005 | Kusaka et al. | | |
| 2008/0146541 A1* | 6/2008 | Wu | ........................... | A61P 1/08 514/211.13 |
| 2011/0218213 A1* | 9/2011 | Royster, Jr. | .......... | A61K 31/195 514/289 |

FOREIGN PATENT DOCUMENTS

| | | |
|---|---|---|
| EP | 2692352 A1 | 2/2014 |
| JP | H04506080 | 10/1992 |
| JP | 2005-232085 | 9/2005 |
| JP | 2007-500755 A | 1/2007 |
| JP | 2008-195728 A | 8/2008 |
| KR | 20180035307 A * | 4/2018 |
| WO | 2002/060279 A1 | 8/2002 |
| WO | 2004/112803 A1 | 12/2004 |
| WO | 2008/140041 A1 | 11/2008 |
| WO | 2012/133825 A1 | 10/2012 |

OTHER PUBLICATIONS

Ferrari (Menopause-related hot fashes and night sweats can last for years, Feb. 23, 2015) (Year: 2015).*
Orosco et al. (Behavioural Brain Research 148 (2004) 1-10) (Year: 2004).*
Turhan et al. (Journal of Food Science, vol. 69, Nr. 2, 2004) (Year: 2004).*
Freedman, J Steroid Biochem Mol Biol. Jul. 2014 ; 142: 115-120 (Year: 2014).*
Intellectual Property Office of Singapore, Office Action Issued In Connection With Singapore Application No. 11201708162U, dated Jun. 19, 2018 (6 pages).
English translation of PCT International Search Report issued in connection with PCT application No. PCT/JP2016/061265, filed Apr. 6, 2016, dated Jun. 28, 2016 (2 pages).
English machine translation of International PCT Publication No. WO2008140041A1, dated Nov. 20, 2008 (31 pages).
Ichikawa, Junji; et al., "Effect of antipsychotic drugs on extracellular serotonin levels in rat medial prefrontal cortex and nucleus accumbens", European Journal of Pharmacology. 1998 ; vol. 351, No. 2 pp. 163-171.
Kehne, J.H.; et al., "Preclinical characterization of the potential of the putative atypical antipsychotic MDL 100,907 as a potent 5-HT2A antagonist with a favorable CNS safety profile", Journal of Pharmacology and Experimental Therapeutics. 1996. vol. 277, No. 2. pp. 968-981.

* cited by examiner

*Primary Examiner* — Sergio Coffa (74) *Attorney, Agent, or Firm* — Lucas & Mercanti, LLP (57) ABSTRACT

The present invention relates to hot flash-suppressing agents and menopausal disorder-improving agents and a food and drink and a pharmaceutical preparation for suppressing hot flash, containing α-lactalbumin as an active ingredient.

8 Claims, 4 Drawing Sheets

HOT FLASH-SUPPRESSING AGENT

CROSS-REFERENCE TO RELATED APPLICATIONS

This application is a 371 of PCT/JP2016/061265, filed Apr. 6, 2016, which claims the benefit of Japanese Patent Application No. 2015-078574, filed Apr. 7, 2015.

TECHNICAL FIELD

The present invention relates to a hot flash-suppressing agent.

BACKGROUND ART

Hot flash is one of typical symptoms of menopausal disorder. Symptoms of menopausal disorder, such as hot flash, are treated by administration of Kampo medicine or hormone replacement therapy. However, the administration of Kampo medicine has some problems, for example, that patients do not take the medicine as directed by a physician because of its distinct flavor. The hormone replacement therapy also has a problem of causing side effects, such as nausea and increased risk of developing cancer.

Patent Literature 1 describes an agent for preventing/treating hot flash, comprising a non-peptidic compound as an active ingredient. Patent Literature 2 also describes hot flash-suppressing agents comprising various plant extracts as active ingredients. However, there is further need for the development of an agent for preventing/treating hot flash, which is easily taken by all patients and is more safe and effective.

Patent Literature 3 states that α-lactalbumin selectively inhibits cyclooxygenase-2 (COX-2) and has an anti-inflammatory analgesic effect (anti-inflammatory action) based on the selective inhibition of COX-2. However, Patent Literature 3 does not disclose anything beyond that α-lactalbumin has an anti-inflammatory action based on the selective inhibition of COX-2. Patent Literature 4 states that α-lactalbumin has a prebiotic effect. However, Patent Literature 4 does not describe other effects of α-lactalbumin.

CITATION LIST

Patent Literature

Patent Literature 1: Japanese Publication No. 2008-195728
Patent Literature 2: International Publication No. WO2012/133825
Patent Literature 3: International Publication No. WO2008/140041
Patent Literature 4: International Publication No. WO2002/060279

SUMMARY OF INVENTION

Technical Problem

An object of the present invention is to provide a hot flash-suppressing agent, which is easily taken by patients and is more safe and effective.

Solution to Problem

As a result of intensive studies for solving the above-described problems, the present inventors have found that α-lactalbumin as a milk protein rich in meal experiences exerts a hot flash-suppressing action, thereby accomplishing the present invention.

Thus, the present invention encompasses the followings.
[1] A hot flash-suppressing agent comprising α-lactalbumin as an active ingredient.
[2] The hot flash-suppressing agent according to [1] above, which is for suppressing hot flash as a symptom of menopause or menopausal disorder.
[3] The hot flash-suppressing agent according to [1] or [2] above, wherein the agent is in a unit packaging form comprising an effective amount of α-lactalbumin.
[4] A menopausal disorder improving agent, comprising the hot flash-suppressing agent according to [1] or [2] above.
[5] The menopausal disorder improving agent according to [4] above, wherein the agent is in a unit-dose packaging form comprising an effective amount of α-lactalbumin.
[6] A method for suppressing hot flash, comprising administering α-lactalbumin or the hot flash-suppressing agent according to any one of [1] to [3] above to a subject.
[7] The method according to [6] above, wherein the subject has a symptom of menopausal disorder.
[8] A method for improving menopausal disorder, comprising administering the menopausal disorder improving agent according to [4] or [5] above to a subject.
[9] A food or drink for suppressing hot flash, comprising α-lactalbumin as an active ingredient or comprising the hot flash-suppressing agent according to any one of [1] to [3] above.
[10] A pharmaceutical preparation for suppressing hot flash, comprising α-lactalbumin as an active ingredient or comprising the hot flash-suppressing agent according to any one of [1] to [3] above.

The present specification encompasses the disclosure of Japanese Patent Application No. 2015-078574 of which the present application claims the priority.

Advantageous Effects of Invention

According to the present invention, a hot flash symptom can be effectively suppressed.

DESCRIPTION OF EMBODIMENTS

The present invention will be described below in detail.

The present invention relates to a hot flash-suppressing agent comprising α-lactalbumin as an active ingredient.

α-Lactalbumin is a major component of the proteins in animal milk (mammalian milk), such as cow milk, as with casein, β-lactoglobulin, lactoferrin, and the like. α-Lactalbumin is an acidic protein of about 14 kDa, and contained at a high concentration in dairy products and whey. α-Lactalbumin used in the present invention may be any α-lactalbumin derived from mammals (human, cow, sheep, goat, pig, or the like) and it is preferably α-lactalbumin derived from bovine milk (cow milk) (bovine α-lactalbumin). The amino acid sequence of the precursor of bovine α-lactalbumin is publicly available under accession numbers J05147 and AAA30367 in the NCBI database and positions 1 to 19 of the full-length amino acid sequence (142 amino acids in length) form a signal peptide, and positions 20 to 142 form the amino acid sequence of the mature protein. A mutant bovine α-lactalbumin in which arginine (R) at position 29 of the amino acid sequence is substituted with glutamine (Q) is also known to be present ("miruku sogoh-jiten" (comprehensive milk dictionary), p. 35, Asakura Publishing Co., Ltd.). α-Lactalbumin secreted into milk is a mature type resulting from the cleavage of the signal peptide moiety from its precursor. In the present invention, α-lactalbumin typically means mature-type α-lactalbumin, containing no signal peptide.

α-Lactalbumin can be prepared from mammalian milk, particularly animal milk or its processed products by a known technique, such as ammonium sulfate precipitation method, an ultrafiltration method, or an ion exchange method. The content of α-lactalbumin in cow milk varies slightly depending on the production area, the feed, and the like; however, the content of α-lactalbumin in Japanese domestic cow milk is typically about 1.2 g/kg, and the use of cow milk as a raw material enables the easy preparation of a large amount of α-lactalbumin. α-Lactalbumin can be synthesized by a chemical method based on the amino acid sequence and the nucleotide sequence, or can be prepared by genetic engineering methods well-known to those skilled in the art. Commercially available α-lactalbumin (e.g., Sigma or Davisco) may also be used as α-Lactalbumin.

As shown in Examples to be described later, α-lactalbumin is capable of effectively suppressing hot flash and can be used as an active ingredient of a hot flash-suppressing agent.

According to the present invention, "hot flash" refers to a chronically or repetitively occurring symptom in which the skin of the face or body has abnormal heat near the surface thereof. Here, "having abnormal heat" refers to, for example, development of heat by a factor that is different from exogenous factors, such as a rise in ambient temperature and the use of a heater, and transient factors, such as fever associated with infection or inflammation, sunburn, heat attack, exercise, and psychological stress, or development of heat exceeding the normal level by e.g., the transient factors. Hot flash appears as a symptom of other diseases involving abnormalities of the autonomic nervous system, such as autonomic imbalance, Basedow disease, alcohol dependence, and diabetes, as well as appearing as a typical symptom of menopausal disorder.

The hot flash-suppressing agent according to the present invention is capable of suppressing hot flash associated with symptoms of other diseases involving abnormalities of the autonomic nervous system, such as Basedow disease, alcohol dependence, and diabetes, as well as suppressing hot flash as a symptom of menopausal disorder, in subjects administered (ingesting) an effective amount of α-lactalbumin contained in the agent. Thus, for example, the present invention provides a method for suppressing hot flash, comprising administering the hot flash-suppressing agent according to the present invention at a dose corresponding to an effective amount of α-lactalbumin to a subject.

The hot flash-suppressing agent according to the present invention can target hot flash associated with symptoms of other diseases involving abnormalities of the autonomic nervous system, such as Basedow disease, alcohol dependence, and diabetes, and can preferably target hot flash as a symptom of menopausal disorder, for suppression.

In the context of the present invention, "suppressing" hot flash means improving a condition of hot flash from a state in which hot flash has already occurred, or a state in which hot flash can occur (menopausal disorder or the like), and includes alleviating the level of hot flash or preventing the occurrence of hot flash.

As stated in Examples to be described later, the effect of suppressing hot flash can be determined (evaluated) using changes over time in skin temperature as an indicator. For example, using ovariectomized rats to which yohimbine is administered (yohimbine administration model), the effect of suppressing hot flash can be determined by measuring the extent of being capable of suppressing a rise in the skin temperature of the tail base of the rat with time while comparing a state in which a test substance is administered with a state in which the test substance is not administered (a state in which water is administered in place of the test substance). Specifically, using the yohimbine administration model, the average skin temperature rise from 10 minutes after to 80 minutes after yohimbine administration is evaluated using, as a reference, skin temperature immediately before yohimbine administration, while comparing a state in which a test substance is administered (a test substance administration group) and a state in which the test substance is not administered (a control group). Then, if the average skin temperature rise in a test substance administration group relative to a control group is 70% or less, preferably 65% or less, more preferably 60% or less, still more preferably 55% or less, the test substance is determined as having a hot flash-suppressing effect.

The hot flash-suppressing agent according to the present invention may be a composition containing a pharmacological component having a different pharmacological activity or the like in addition to α-lactalbumin.

The hot flash-suppressing agent according to the present invention can be used for suppressing hot flash without resort to a cyclooxygenase-2 (COX-2) inhibitory action and an anti-inflammatory action based thereon, and preferably can be used for suppressing hot flash as a symptom of menopausal disorder. Thus, for example, the present invention also provides a menopausal disorder improving agent, comprising the hot flash-suppressing agent according to the present invention. Herein, the menopausal disorder improving agent, comprising the hot flash-suppressing agent according to the present invention may be a composition containing a pharmacological component having a different pharmacological activity in addition to a hot flash-suppressing agent having a menopausal disorder improving action. The present invention also provides a method for improving menopausal disorder, comprising administering the menopausal disorder improving agent to a subject. In the context of the present invention, improving menopausal disorder refers to improving, reducing, or eliminating symptoms of menopausal disorder, including hot flash. The hot flash-suppressing agent according to the present invention can also be used for reducing the risk of causing hot flash, for example, hot flash as a symptom of menopausal disorder. Thus, the hot flash-suppressing agent according to the present invention can also be used as one component of an agent for treating/preventing various diseases involving hot flash. The hot flash-suppressing agent according to the present invention may be parenterally, for example, enterally, administered (ingested), or may be orally administered; however, the agent is preferably administered orally.

Examples of a subject for administration of the hot flash-suppressing agent according to the present invention include any mammals (subjects) including human, domestic animals (e.g., horse, cow, sheep, goat, and pig), pet animals (e.g., dog, cat, and rabbit), and experimental (test) animals (e.g., mouse, rat, and monkey); and preferred examples thereof include mammals having hot flash and mammals having diseases prone to or predisposition to develop hot flash.

Dosage or ingestion dose of the hot flash-suppressing agent according to the present invention can be set appropriately in light of various factors, such as administration route, the age, body weight, and symptoms of a subject. The dosage or ingestion dose set may be preferably, for example, 30 mg to 10 g, preferably 50 mg to 5 g, more preferably 100 mg to 2 g of α-lactalbumin to be dosed or ingested, per administration or ingestion. The hot flash-suppressing agent according to the present invention may be administered as single dose, or may be administered as multiple doses at intervals of several hours to several months.

The hot flash-suppressing agent according to the present invention is preferably packed in a unit dose (a single ingestion dose) (i.e., being in a unit-dose packaging form) in view of hygiene at its administration (ingestion) and ease of handling during its transportation/storage. Thus, for example, the present invention provides a hot flash-suppressing agent in a unit-dose packaging form. In the context of the present invention, the "unit-dose packaging form" may be a form packed in a unit dose per administration or ingestion. The unit dose of the hot flash-suppressing agent according to the present invention per administration or ingestion is, for example, 5 g to 500 g (or 5 mL to 500 mL), preferably 10 g to 300 g (or 10 mL to 300 mL), more preferably 50 g to 200 g (or 50 mL to 200 mL). The unit dose of the hot flash-suppressing agent according to the present invention per ingestion may be a daily dose or, for example, may be a divided dose that corresponds to ½ to ¹⁄₁₀ aliquot of the daily dose.

The hot flash-suppressing agent according to the present invention can be incorporated (added) into a pharmaceutical preparation or a food or drink, and can also be used in combination with a pharmaceutical preparation or a food or drink. Thus, for example, the present invention also provides a pharmaceutical preparation or a food or drink comprising the hot flash-suppressing agent according to the present invention, and a set of a pharmaceutical preparation or a food or drink in combination with the hot flash-suppressing agent according to the present invention. The pharmaceutical preparation or the food or drink comprising the hot flash-suppressing agent according to the present invention, or the pharmaceutical preparation or the food or drink in combination with the hot flash-suppressing agent according to the present invention can be used for suppressing hot flash by administration to (or ingestion by) a subject as described above.

The present invention also provides a pharmaceutical preparation and a food or drink comprising α-lactalbumin as an active ingredient. The pharmaceutical preparation and the food or drink are, preferably, for suppressing hot flash. In a preferred embodiment, the pharmaceutical preparation and the food or drink of the present invention may be for suppressing hot flash as a symptom of menopausal disorder and for thereby improving menopausal disorder. The pharmaceutical preparation and the food or drink of the present invention may be for reducing the risk of developing hot flash, for example, hot flash as a symptom of menopausal disorder.

The pharmaceutical preparation according to the present invention may further contain pharmaceutically acceptable auxiliary for the preparation (for example, inert carrier such as solid or liquid carrier, excipient, surfactant, binder, disintegrant, lubricant, solubilizer, suspending agent, coating agent, colorant, flavoring agent, preservative, buffering agent, and pH adjuster) or the like as a pharmacological component having a different pharmacological activity or the like. Specifically, the pharmaceutical preparation according to the present invention may further comprise, for example, water, another aqueous solvent, a pharmaceutically acceptable organic solvent, collagen, polyvinyl alcohol, polyvinylpyrrolidone, carboxyvinyl polymer, alginate sodium, water-soluble dextran, water-soluble dextrin, sodium carboxymethyl starch, pectin, xanthan gum, gum Arabic, casein, gelatin, agar, glycerin, propylene glycol, polyethylene glycol, vaseline, paraffin, stearyl alcohol, stearic acid, human serum albumin, mannitol, sorbitol, or lactose, or artificial cell structures, such as liposomes. The auxiliary substances or the like for the preparation can be appropriately selected depending on the dosage form of the preparation. The pharmaceutical preparation according to the present invention may further comprise vitamins, minerals, saccharides, amino acids, peptides, an antibiotic, or the like, at their adequate amounts.

The pharmaceutical preparation according to the present invention may be one formulated into any dosage form, including solid preparations, such as tablets, granules, powders, pills, and capsules, liquid preparations, such as solutions, suspensions, and syrups, gels, and aerosols. When the pharmaceutical preparation is used as a liquid preparation, it can also be formulated as a dried product intended to be reconstituted, immediately before use, for example, with saline. The pharmaceutical preparation according to the present invention can be appropriately set for the content of t-lactalbumin in the preparation, and the content can vary, for example, depending on the dosage form, auxiliary substances for the preparation, and the severity of a disease of a subject.

The food or drink according to the present invention may further comprise, for example, auxiliary substances for preparation, acceptable in the art of manufacturing food and drink (e.g., inert carrier such as solid or liquid carrier, excipient, surfactant, binder, disintegrant, lubricant, solubilizer, suspending agent, coating agent, colorant, flavoring agent, preservative, buffering agent, and pH adjuster). Specifically, the food or drink according to the present invention may further comprise, for example, water, protein, saccharide, lipid, vitamins, minerals, organic acid, organic base, fruit juices, or flavors.

In the present invention, examples of a raw material of the protein include animal proteins, such as whole powdered milk, powdered skim milk, partially-skimmed milk powder, whole concentrated milk, concentrated skim milk, partially-skimmed concentrated milk, casein (α-casein, β-casein, and κ-casein), whey, demineralized whey, whey powder, demineralized whey powder, whey protein, whey protein concentrate (WPC), whey protein isolate (WPI), β-lactoglobulin, lactoferrin, chicken egg protein, and meat protein; plant proteins, such as soy protein; degradation products thereof; peptides, such as casein phosphopeptide, and amino acids, such as arginine and lysine. In the present invention, examples of a raw material of the saccharide include, for example, lactose, saccharides, processed starch (soluble starch, British starch, oxidized starch, starch ester, starch ether, or the like, as well as dextrin), and dietary fiber. In the present invention, examples of a raw material of the lipid include animal fat and oils, such as butter, cream, phospholipid, lard, and fish oil, and fractionated oils, hydrogenated oils, and transesterified oils thereof; plant fat and oils, such as palm oil, safflower oil, corn oil, rapeseed oil, coconut oil, and fractionated oils, hydrogenated oils, and transesterified oils thereof. These substances or components may be used alone or in a combination of two or more thereof. These substances or components may be synthesized ones or naturally occurring ones.

In the present invention, examples of raw materials of vitamins include, for example, non-protein nitrogen, sialic acid, vitamin A, carotenes, B vitamins, vitamin C, D vitamins, vitamin E, K vitamins, vitamin P, vitamin Q, niacin, nicotinic acid, pantothenic acid, biotin, inositol, choline, and folic acid. In the present invention, examples of raw materials of the minerals include, for example, whey minerals, calcium, potassium, magnesium, sodium, copper, iron, manganese, zinc, and selenium. In the present invention, a raw material of the organic acid include, for example, malic acid, citric acid, lactic acid, tartaric acid, and erythorbic acid. These substances or components may be used alone or in a combination of two or more thereof. These substances or components may be synthesized ones or naturally occurring ones.

The food or drink according to the present invention may be in any form, such as dairy product, processed food, prepared food, confectionery, seasoning, and beverage. The food or drink according to the present invention is preferably in the form of a functional food. The food or drink according to the present invention may be, for example, a supplement for humans in a state in which hot flash has already occurred or in a state in which hot flash can occur (menopausal disorder or the like).

In the context of the present invention, the "functional food" refers to a food capable of imparting predetermined functionality to a living body, and includes any health foods, such as foods for specified health use (including a conditional foods for specified health use), foods with function claims, foods with health claims such as foods with nutrient function claims, special-use foods, nutritional supplementary foods, health supplements, supplements (e.g., in various dosage forms, such as tablets, coated tablets, sugar-coated tablets, capsules, and solutions), and beauty foods (e.g., diet foods). In the context of the present invention, the "functional food" includes health foods with health claims based on the food standards of CODEX (FAO/WHO Joint Food Standards Committee).

The food or drink according to the present invention may be prepared in any form, such as solid, solution, mixture, suspension, paste, gel, powder, granule, or capsule. The hot flash-suppressing agent or α-lactalbumin according to the present invention may be incorporated into the food or drink according to the present invention by any adequate method available to those skilled in the art. Specifically, in the food or drink according to the present invention, the hot flash-suppressing agent or α-lactalbumin may be encapsulated, or the hot flash-suppressing agent or α-lactalbumin may be wrapped by an edible film, an edible coating agent, or the like; or, the food or drink according to the present invention may be formed into any form, such as tablet, after mixing (adding) an adequate excipient or the like with the hot flash-suppressing agent or α-lactalbumin. The food or drink according to the present invention may be produced by processing a composition containing the hot flash-suppressing agent or α-lactalbumin according to the present invention and other food materials. Then, in the food or drink according to the present invention, for example, the hot flash-suppressing agent or α-lactalbumin can be incorporated (added) into various foods (e.g., cow milk, soft drink, fermented milk, yogurt, cheese, bread, biscuits, crackers, pizza crust, prepared milk powder, liquid diets, foods for sick, nutritional foods, frozen foods, processed foods, and other commercial foods), or the various foods can be used in combination with the hot flash-suppressing agent or α-lactalbumin. The pharmaceutical preparation or the food or drink according to the present invention may comprise the hot flash-suppressing agent according to the present invention or α-lactalbumin at the above-mentioned dose per administration or ingestion.

For pharmaceutical preparation or the food and drink according to the present invention, the subject for the administration can be set in a similar way to the subject for the administration of the hot flash-suppressing agent.

The present invention also includes the followings (1) to (6).

(1) A method for suppressing hot flash (improving menopausal disorder), comprising a step of (orally) administering to a subject (or having a subject ingest) a-lactalbumin or a composition (agent) comprising α-lactalbumin.

(2) Use of α-lactalbumin in the manufacture of a hot flash-suppressing agent.

(3) α-Lactalbumin for use in suppressing hot flash.

(4) A method for producing a hot flash-suppressing agent, comprising a step of combining α-lactalbumin with a pharmaceutically acceptable carrier.

(5) A composition (agent) comprising α-lactalbumin, which is for use as an additive to a pharmaceutical preparation (a pharmaceutical composition) or a food or drink (a food or drink composition) and for use in suppressing hot flash.

(6) A method for providing a hot flash-suppressing effect to a pharmaceutical composition, a nutritional pharmaceutical composition, a pharmaceutical preparation, a drug, a food or drink composition, a food or drink, a nutritional composition, a special-use food, a food with nutrient function claims, a health food, or the like, comprising a step of adding (incorporating) α-lactalbumin or a composition containing α-lactalbumin to the pharmaceutical composition, the nutritional pharmaceutical composition, the pharmaceutical preparation, the drug, the food or drink composition, the food or drink, the nutritional composition, the special-use food, the food with nutrient function claims, the health food, or the like.

EXAMPLES

The present invention will be more specifically described below with reference to Examples. However, these Examples are not intended to limit the technical scope of the present invention.

Example 1

An ovariectomized rat to which yohimbine is administered (yohimbine administration model) is used as a hot flash model. This Example examined whether α-lactalbumin (α-La) has an effect of suppressing a rise in skin temperature (hot flash), using the yohimbine administration model.

The ovary was removed from 7-week old female SD rats (Japan SLC Inc.) to prepare animal models of menopausal disorder, which were then used for an experiment after 1 week. In this experiment, the rats were divided into 3 groups (n=6 per group) with comparable mean body weight.

Distilled water for injection was orally administered at 10 mL/kg body weight to a normal group and a control group. α-La was orally administered at 300 mg/kg body weight (as 10 mL/kg body weight of an α-La solution in distilled water for injection) to an α-La administration group.

After 30 minutes from the oral administration, distilled water for injection was subcutaneously administered at 2 mL/kg body weight to the normal group, and yohimbine was subcutaneously administered at 2 mg/kg body weight (2 mL/kg body weight of yohimbine solution in distilled water for injection) to the control group and the α-La administration group. In addition, the skin temperature of the tail base of the rat was measured with time every 5 minutes from immediately after to 80 minutes after the subcutaneous administration.

Figure 1:
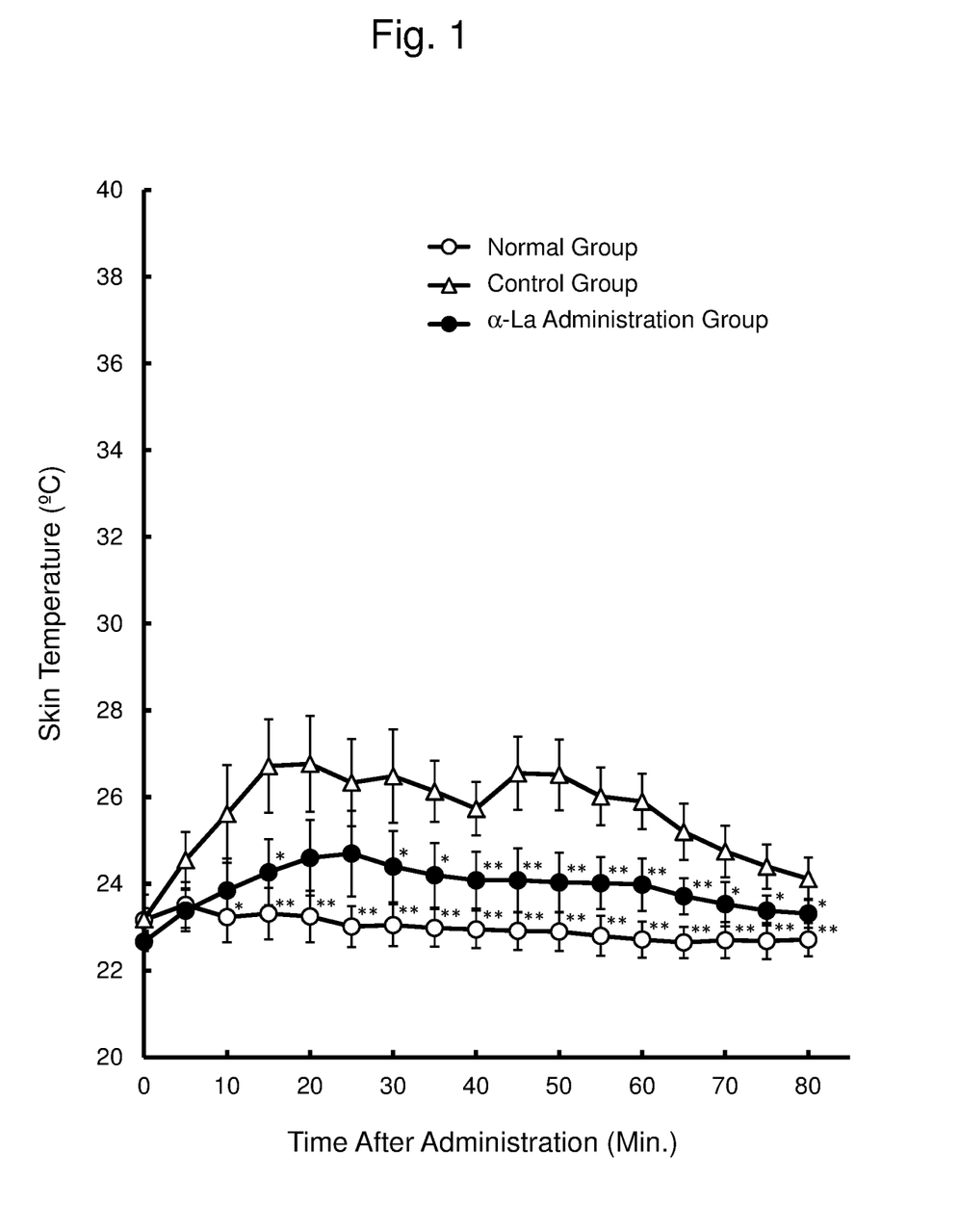
FIG. 1 is a graph of changes over time in the skin temperature of the tail base of the rat, showing the effect of α-lactalbumin (α-La) administration. In the figure, the white circle indicates the result of a normal group; the white triangle indicates the result of a control group (administration of water+yohimbine); and the black circle indicates the result of an α-La administration group (administration of α-lactalbumin+yohimbine). * denotes statistical significance at $p<0.05$, and ** denotes statistical significance at $p<0.01$, relative to the control group.

Changes over time in the skin temperature of the tail base of the rat are shown in FIG. 1. In the normal group, the skin temperature hardly rose. In the control group, the skin temperature rose with time by the action of yohimbine. In contrast, in the α-La administration group, the effect of yohimbine was suppressed and a rise in the skin temperature was significantly suppressed, compared to the control group.

These results showed that a rise in skin temperature (hot flash) is suppressed by the effect of α-La.

Example 2

The inhibition of cyclooxygenase-2 (COX-2) is known as one of the action mechanisms of the anti-inflammatory effect of α-lactalbumin (α-La). Thus, this Example examined whether COX-2 inhibition has an effect of suppressing a rise in skin temperature (hot flash), using a yohimbine administration model. In this examination, celecoxib was used as a selective COX-2 inhibitor.

The ovary was removed from 7-week old female SD rats (Japan SLC Inc.) to prepare animal models of menopausal disorder, which were then used for an experiment after 1 week. In this experiment, the rats were divided into 3 groups (n=6 per group) with comparable mean body weight.

A gum arabic solution (1% by weight) was orally administered at 10 mL/kg body weight to a normal group and a control group. Celecoxib was orally administered at 10 mg/kg body weight (as 10 mL/kg body weight of a dispersion of celecoxib in a gum arabic solution (1% by weight)) to a celecoxib administration group. The gum arabic solution was used to enhance the dispersibility of celecoxib.

After 30 minutes from the oral administration, distilled water for injection was subcutaneously administered at 2 mL/kg body weight to the normal group, and yohimbine was subcutaneously administered at 2 mg/kg body weight (as 2 mL/kg body weight of a yohimbine solution in distilled water for injection) to the control group and the α-La administration group. In addition, the skin temperature of the tail base of the rat was measured with time every 5 minutes from immediately after to 80 minutes after the subcutaneous administration.

Figure 2:
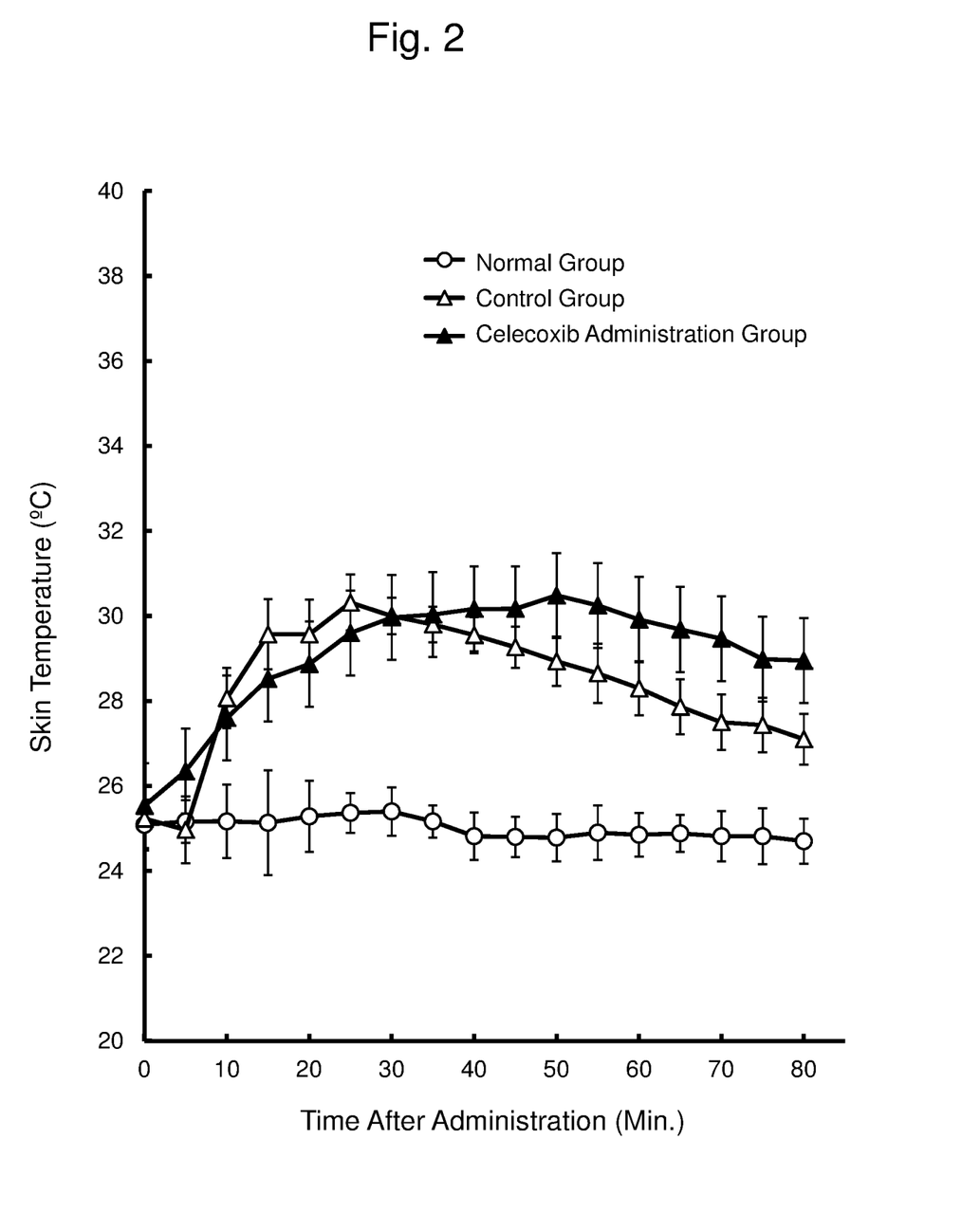
FIG. 2 is a graph of changes over time in the skin temperature of the tail base of the rat, showing the effect of celecoxib administration. In the figure, the white circle indicates the result of a normal group; the white triangle indicates the result of a control group (administration of water+yohimbine); and the black triangle indicates the result of a celecoxib administration group (administration of celecoxib+yohimbine).

Changes over time in the skin temperature of the tail base of the rat are shown in FIG. 2. In the normal group, the skin temperature hardly rose. In the control group, the skin temperature rose with time by the action of yohimbine. In the celecoxib administration group, the skin temperature also rose with time without the suppression of yohimbine action, compared to that in the control group.

These results showed that the cyclooxygenase-2 (COX-2)-inhibiting action of celecoxib could not suppress a rise in skin temperature (hot flash). In other words, it was shown that the COX-2-inhibiting effect of α-La providing an anti-inflammatory effect cannot suppress a rise in skin temperature (hot flash) and the skin temperature rise (hot flash)-suppressing effect of α-La is due to a distinct mechanism from COX-2 inhibition.

Example 3

β-Lactoglobulin (β-Lg) is a typical whey protein (milk protein) different from α-lactalbumin (α-La). This Example examined whether β-lactoglobulin (β-Lg) has an effect of suppressing a rise in skin temperature (hot flash), using a yohimbine administration model.

The ovary was removed from 7-week old female SD rats (Japan SLC Inc.) to prepare animal models of menopausal disorder, which were then used for an experiment after 1 week. In this experiment, the rats were divided into 2 groups (n=4 per group) with comparable mean body weight.

Distilled water for injection was orally administered at 10 mL/kg body weight to a control group. β-Lg was orally administered at 300 mg/kg body weight (as 10 mL/kg body weight of a β-Lg solution in distilled water for injection) to a β-Lg administration group.

After 30 minutes from the oral administration, yohimbine was subcutaneously administered at 2 mg/kg body weight (as 2 mL/kg body weight of a yohimbine solution in distilled water for injection) to the control group and the β-Lg administration group. In addition, the skin temperature of the tail base of the rat was measured with time every 5 minutes from immediately after to 80 minutes after the subcutaneous administration.

Figure 3:
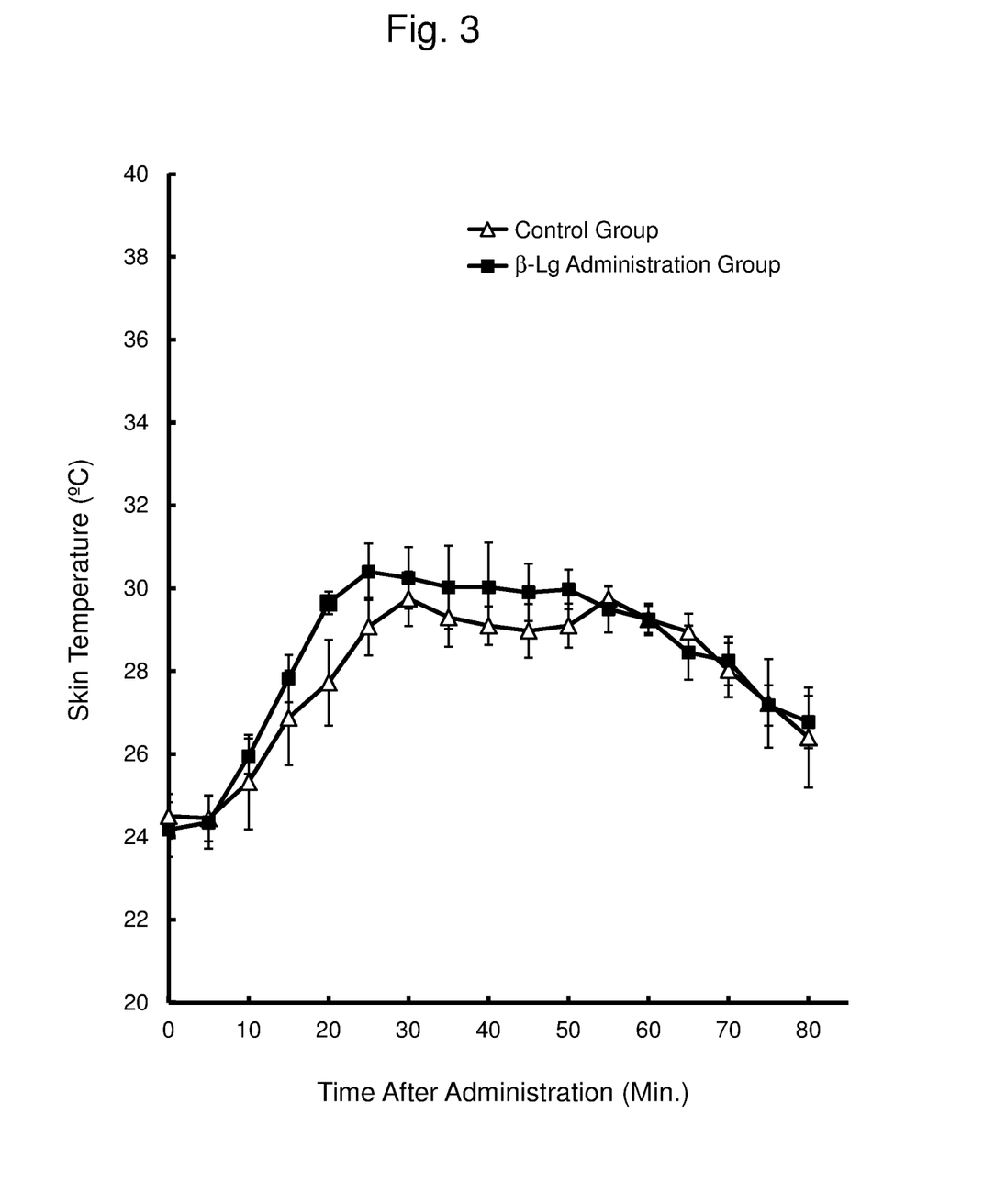
FIG. 3 is a graph of changes over time in the skin temperature of the tail base of the rat, showing the effect of β-lactoglobulin (β-Lg) administration. In the figure, the white triangle indicates the result of a control group (administration of water+yohimbine), and the black square indicates the result of a β-Lg administration group (administration of β-lactoglobulin+yohimbine).

Changes over time in the skin temperature of the tail base of the rat are shown in FIG. 3. In the control group, the skin temperature rose with time by the action of yohimbine. In the β-Lg administration group, the skin temperature also rose with time without the suppression of yohimbine action, compared to that in the control group.

These results showed that a whey protein different from α-La, such as β-Lg, cannot suppress a rise in skin temperature (hot flash). In other words, it was shown that the effect of suppressing a rise in skin temperature (hot flash) was observed for not every milk protein and specifically observed for α-La.

Eample 4

Keisibukuryogan is a typical Kampo preparation (harbal medicine) intended for improving menopausal disorder. This Example examined whether keisibukuryogan has an effect of suppressing a rise in skin temperature (hot flash) using a yohimbine administration model.

The ovary was removed from 7-week old female SD rats (Japan SLC Inc.) to prepare animal models of menopausal disorder, which were then used for an experiment after 1 week. In this experiment, the rats were divided into 2 groups (n=5 per group) with comparable mean body weight.

Distilled water for injection was orally administered at 10 mL/kg body weight to a control group. Keisibukuryogan was orally administered at 1 g/kg body weight (as 10 mL/kg body weight of a keisibukuryogan solution in distilled water for injection) to a Kampo preparation administration group.

After 30 minutes from the oral administration, yohimbine was subcutaneously administered at 2 mg/kg body weight (as 2 mL/kg body weight of a yohimbine solution in distilled water for injection) to the control group and the Kampo preparation administration group. In addition, the skin temperature of the tail base of the rat was measured with time every 5 minutes from immediately after to 80 minutes after the subcutaneous administration.

Figure 4:
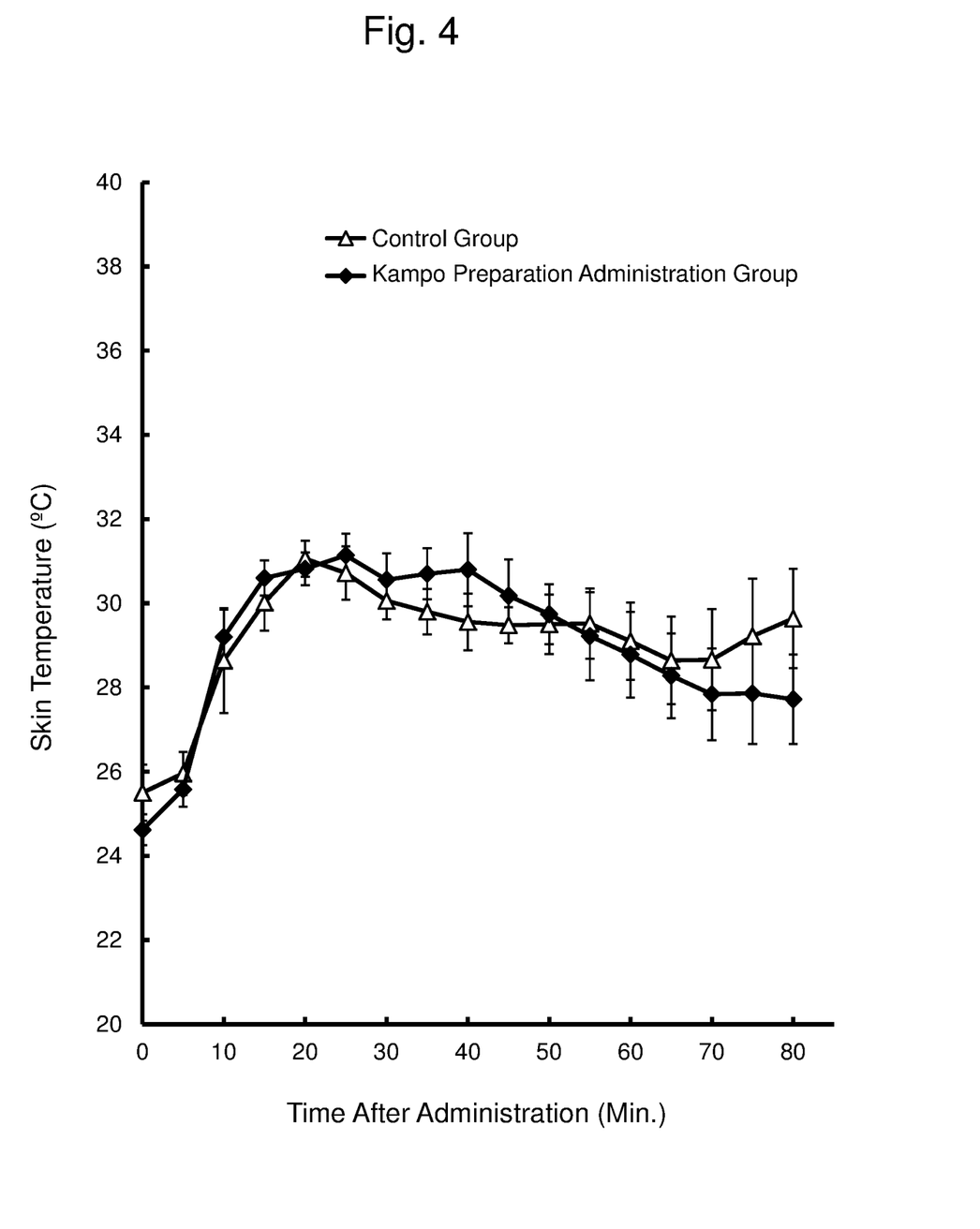
FIG. 4 is a graph of changes over time in the skin temperature of the tail base of the rat, showing the effect of Kampo preparation (keisibukuryogan) administration. In the figure, the white triangle indicates the result of a control group (administration of water+yohimbine), and the black rhombus indicates the result of a Kampo preparation administration group (administration of keisibukuryogan+yohimbine).

Changes over time in the skin temperature of the tail base of the rat are shown in FIG. 4. In the control group, the skin temperature rose with time by the action of yohimbine. Also in the Kampo preparation administration group, the skin temperature rose with time without the suppression of yohimbine action, compared to that in the control group.

These results showed that a Kampo preparation intended for improving menopausal disorder, such as keisibukuryogan, cannot suppress a rise in skin temperature (hot flash). As seen above, the effect of suppressing a rise in skin temperature (hot flash) was observed in the single administration of α-La, while the hot flash-suppressing effect was not observed in the single administration of the Kampo preparation, showing that even a preparation for improving menopausal disorder was not always effective in suppressing hot flash.

INDUSTRIAL APPLICABILITY

The present invention can be used in producing a food and drink and a pharmaceutical preparation useful for improving hot flash, and particularly can be used in producing a food and drink and a pharmaceutical preparation useful for improving hot flash as a symptom of menopause.

All publications, patents, and patent applications cited in this application are intended to be incorporated herein by reference in their entirety.

The invention claimed is:

1. A method for suppressing a hot flash in a subject in need thereof, the method comprising administering to the subject a composition consisting essentially of an effective amount of α-lactalbumin as the only active ingredient for treating hot flashes.

2. The method according to claim 1, wherein the hot flash is a symptom of menopause.

3. The method according to claim 1, wherein α-lactalbumin is in a unit-dose packaging form comprising an effective amount of α-lactalbumin.

4. The method according to claim 1, wherein the amount of administered α-lactalbumin is from 30 mg to 10 g.

5. The method according to claim 4, wherein the amount of administered α-lactalbumin is from 50 mg to 5 g.

6. The method according to claim 5, wherein the amount of administered α-lactalbumin is from 100 mg to 2 g.

7. The method according to claim 1, wherein the composition is a pharmaceutical composition.

8. The method according to claim 1, wherein the composition is a food or drink.

* * * * *